United States Patent [19]

Schnepp-Pesch et al.

[11] Patent Number: 5,195,954
[45] Date of Patent: Mar. 23, 1993

[54] APPARATUS FOR THE REMOVAL OF DEPOSITS IN VESSELS AND ORGANS OF ANIMALS

[76] Inventors: Wolfram Schnepp-Pesch, Schönblick 6, D-7505 Ettlingen; Josef Lindenberg, Käthe-Kollwitz-Str. 10a, D-7500 Karlsruhe, both of Fed. Rep. of Germany

[21] Appl. No.: 543,428

[22] Filed: Jun. 26, 1990

[51] Int. Cl.⁵ .............................................. A61B 17/32
[52] U.S. Cl. ..................................... 604/22; 606/159; 606/127; 606/170
[58] Field of Search ............... 606/180, 170, 159, 128, 606/127; 604/22

[56] References Cited

U.S. PATENT DOCUMENTS

| | | | |
|---|---|---|---|
| 3,614,953 | 10/1971 | Moss | 606/159 |
| 3,937,222 | 2/1976 | Banko | 606/170 |
| 4,030,503 | 6/1977 | Clark | 606/159 |
| 4,745,919 | 5/1988 | Bundy et al. | 606/159 |
| 4,771,774 | 9/1988 | Simpson et al. | 606/180 X |
| 4,784,636 | 11/1988 | Rydell | 606/159 X |
| 4,790,812 | 12/1988 | Hawkins et al. | 606/159 X |
| 4,857,046 | 8/1989 | Stevens et al. | 604/22 |

FOREIGN PATENT DOCUMENTS 1475616 4/1989 U.S.S.R. .................... 604/22

*Primary Examiner*—Michael H. Thaler
*Attorney, Agent, or Firm*—Antonelli, Terry, Stout & Kraus

[57] ABSTRACT

An apparatus for removing deposits, such as patches in vessels and stones in organs of animals is described, which has a hollow guidance part, a motor and a shaft driven by the latter and projecting into the guidance part and which is constructed in such a way that at the distal end (44) of the driving shaft (26) are provided helixes (61,63), which at least partly project out of the distal end (14) of the guidance part (2) and whose cross-sectional dimensions at the most correspond to the internal diameter of said guidance part.

7 Claims, 6 Drawing Sheets

1

APPARATUS FOR THE REMOVAL OF DEPOSITS IN VESSELS AND ORGANS OF ANIMALS

The invention relates to a process and an apparatus for removing deposits, such as patches or plaques in vessels and stones or calculi in organs of living organisms or animals, in which the apparatus has a hollow guidance part, a motor and a shaft driven by the latter and projecting into the guidance part.

BACKGROUND OF THE INVENTION

In the surgical removal of gallstones it is necessary to make a very large incision, which often heals badly and forms large scars. As a result of the high recurrence rate of gallstone formation, it is in many cases necessary to surgically remove the entire gall bladder to avoid the repeated removal of such stones. Quite apart from the fact that such an operation is very unpleasant and requires a long stay in the hospital, it is subject to high risks. It must be carried out under general anesthetic, which always forms a significant risk. It is also impossible to crush and remove by ultrasonic litholapaxy soft stones, such as cholesterin and pigment stones. Attempts have also been made to destroy gallstones by laser beams, but this is not of an optimum nature for all stone types.

Attempts have been made to remove deposits in blood vessels by a knife rotating in a catheter provided with a lateral window. However, satisfactory results have not been obtained.

Normally thrombi are gripped by an atherectomy loop or sling, are crushed as far as possible and drawn out through a guiding catheter and this can be assisted by suction. This process is complicated and requires considerable sensitivity on the part of the surgeon. A separated thrombus part can easily slide out of the loop, be carried on and clog narrower vessels.

Furtheron deposits, such as thrombotic occlusions in vessels or the like may be removed by a rotary element moved in the vessel towards the closing or constriction and with respect to which a rotational speed of about 100,000 r.p.m. has been proposed in order to pulverize the occlusion material. However, there is a risk of the pulverized particles being redeposited at other points and possibly in much narrower, but important vessels, where damage can be caused. Other apparatuses rotating at a lower speed up to max 500 r.p.m. merely move the vessel-closing material to the side. Thus, it is not possible to achieve a reliable, permanent exposure of a stenosis, quite apart from an opening of an occlusion. In addition, apparatuses are known, which cut out constricting material in the vessel in one way or another. To the extent that a rotary catheter is used, the danger exists that it takes the vessel wall with it during its rotation with the associated risk of an entanglement, so that here again it is only possible to operate at very low speeds. To the extent that the removal takes place by working instruments passed through a catheter on a shaft, then the instruments must operate at a distance from the catheter orifice, so that possibly the suction exerted by the catheter will not be adequate for removing all the abraded particles.

SUMMARY OF THE INVENTION

One object of the invention is to provide an apparatus and a process avoiding or at least considerably further reducing the need for gall bladder operations even in the case of soft stones and which makes it possible to remove thrombi and also vasoconstriction caused by deposits.

Another object of the invention is to safely move abraded parts of occlusions towards the catheter orifice, so that they can be reliably suctioned off there by a vacuum applied.

The invention provides an apparatus for removing deposits, such as patches in vessels and stones in organs of animals, with a hollow guidance part, a motor and a shaft driven by the latter and projecting in to the guidance part, in which on the distal end of the driving shaft is arranged a rigid helical attachment, which projects over the distal end of the guidance part and whose cross-sectional dimensions at the most correspond to the internal diameter of the guidance part.

According to the process of the invention the deposits are crushed with a rapidly rotating helix or coil. The terms "distal" and "proximal" are clearly defined in medical technology and in the case of equipment and apparatus relate to the doctor or surgeon (as opposed to body parts, where reference is made to the patient's heart).

In a simple manner, the invention not only makes it possible to remove deposits in vessels, but also takes up deposit parts removed by the helix construction and leads them reliably to and into the distal end of the hollow guidance part. An important advantage of the invention is that the destruction and removal of the deposits can take place under a local anesthetic.

The removal of the deposit parts can in particular be assisted by suction. The invention also makes it possible to destroy gallstones following the puncture of the gall, in that the helical attachment is pressed against such a stone and destroys it by the rotation exerted by the motor via the shaft. Here again suction can be provided.

Like the shaft, the helical attachment is preferably rigid. However, necessarily the shaft is bendable in its area located in the guidance part and once again the helical attachment rotates about its axis due to the shaft being guided by the guidance part.

In a preferred manner, the individual turns of the helical attachment are arranged with a finite spacing from one another. Thus, deposits can be received between the individual turns of the helix and can be reliably lead by the latter to the distal end of the guidance part. This can be further assisted in that the turns of the helical attachment, particularly a spheroid bounded by the inner wall areas thereof surrounds a free space within the helical attachment and then deposits can be conveyed within the helix to the guidance part.

According to another preferred construction a helical attachment is constructed as a screw thread constructed on an axial core and in particular the distal (front) end of the shaft has a blade-like widened portion and the latter is bent about the axis of symmetry of the shaft in a manner corresponding to the screw shape.

The helical attachment can be constructed in different ways. Thus, according to a preferred construction the cross-section of the helical attachment is constant over its height. Such a construction is in particular used when removing deposits in vessels. According to another advantageous construction the helical attachment is conical and in particular tapers towards its distal end. According to a further development, such a construction is provided with a taper towards the distal end, because the helical attachment bores into the stone and can shatter the latter. On widening the helical attachment towards the distal end and which is also fundamentally possible, stone parts could be trapped and jammed in the helical area and then drawn out with the complete helical attachment. According to another construction the distal end of the helical attachment is slightly bent out of the axial direction of the driving shaft. This construction is also particularly advantageous in the destruction of stones, because periodically the bent distal end of the helical attachment then strikes against the stone, so that the latter can be destroyed. The shattering of gallstones is obviously observed preferably by X-ray examination or by ultrasonics.

In order to avoid in a reliable manner any injury, particularly in connection with sensitive blood vessels, according to a further development the distal region of the helical attachment is truncated and, in particular, the distal end of the said attachment is bent over and given the shape of a figure of eight.

While the shaft and the helical attachment can fundamentally be separately constructed and then provided with adapted fastening means, so that in the case of a shaft different attachments can be fitted, according to a preferred development the shaft and helical attachment are constructed in one piece. Preferably, according to a preferred development, the proximal end of the guidance part is sealed against the shaft. Such a construction is advantageous, but is particularly chosen when the guidance part has at the proximal end a branch branching off a lumen receiving the shaft and connectable to a suction device. According to a further development the guidance part has two lumens and besides a main lumen with a cross-section taking up virtually the entire internal cross-sectional area, there is a secondary lumen with a much smaller cross-section and to whose proximal end can be fitted a syringe, possibly via a branch. The deposits can be partly dissolved by streptokinase in this way. Here again the external diameter of the guidance part need not exceed 5 mm and is preferably 3 to 4 mm.

The speed of the driving motor is preferably several hundred revolutions and, in particular, approximately 2,000 r.p.m.

According to a preferred development, the helical attachment can be brought through the guidance part into the vicinity of a deposit and the latter is then removed by rotating the helical attachment.

The invention further provides a drive for an apparatus for removing deposits, such as occlusions in vessels or the like, with a device for receiving the start of an elongated, hollow guide part, such as a catheter, and with a rotary connecting part to the rotary drive of devices for removing deposits upstream of the proximal end of the guide part, which is characterized in that the connecting part can be moved backwards and forwards in the axial direction relative to the guide part receptacle.

As a result of the axially movable construction of the connecting part for the working instruments used for the abrading removal of the deposits and which can have different constructions, it is possible to introduce the instruments for the removal of the material from the catheter orifice in the vicinity of the stenosis or occlusion and, while maintaining the rotation, to rhythmically return the instruments to the catheter orifice and possibly partly into the same, so that particles carried along with the working instruments can be suctioned off by the vacuum exerted in the catheter or in the hollow guide part.

The working instruments driven by the drive can be constructed in different ways. They can be in the form of spiral or basket-shaped constructions, in which the abrading elements are in the form of blunt or tapered wires positioned axially on the circumference of a fictional spheroid. These two constructions collect the material removed in the area resulting from the abrading wires or the screw or helix construction and can reliably carry the same during their return movement to the orifice of the hollow guide part, so that the abrading material is reliably suctioned off. However, fundamentally other constructions of the instruments are possible.

The axial reciprocating movement of the connecting part of the inventive drive and therefore the working instruments connected thereto takes place manually in a preferred construction and advantageously the rotary connecting part is manually axially reciprocatable. Thus, the surgeon can control and set in a desired manner the axial reciprocating movement of the working instruments. Alternatively, in order to make the work of the surgeon easier, the rotary connecting part can be axially reciprocated in motor manner. The axial drive can be constructed in such a way that a sleeve is provided, which is axially fixed, but connected in rotary manner to the connecting part and in non-rotary manner to the drive casing and having a closed groove passed in meander-like manner around the circumference and in which engages the cam of a transmission part rotating at a lower angular velocity than that of the connecting part. The reciprocating movement can be derived from the same motor, which brings about the high-speed rotary movement of some 100 to 2000 r.p.m. of the connecting part and therefore the working instruments, in that between the driven shaft of the motor and the transformation gear for transforming a rotary drive into the linear reciprocating movement, a transmission gear is provided, such as are e.g. known in connection with clockworks.

For the connection of the working instruments via a shaft projecting through the guide part, the connecting part can have a coupling member, e.g. in the form of a Luer-Lok or the like. The hollow, elongated guide part, in particular, a catheter, is firmly connected to the drive in that on the reception means for the same is constructed in the axial direction an inwardly directed circumferential groove bounded on both sides by shoulders and into which can be inserted the radial flange parts of the catheter or elements firmly connected thereto.

The drive preferably has an electric motor and, in order to ensure independence from the mains and also for safety reasons, is provided with its own power storage means. The latter can be a chargeable accumulator or a battery. It is in both cases advantageous for the display means to be a LCD. Thus, the surgeon's attention is in good time drawn to the fact that the power supply of the power storage means is inadequate or that the voltage has dropped, so that he can replace said means in good time instead of being surprised by this phenomenon during an operation. The accumulator is preferably interchangeably arranged in a corresponding compartment in the casing. According to another preferred embodiment, the drive is provided with a speed regulator. It obviously also has an on/off switch.

BRIEF DESCRIPTION OF THE DRAWINGS

Further advantages and features of the invention can be gathered from the claims and the following description relative to non-limitative embodiments and the attached drawings, wherein:

DETAILED DESCRIPTION

Figure 1:
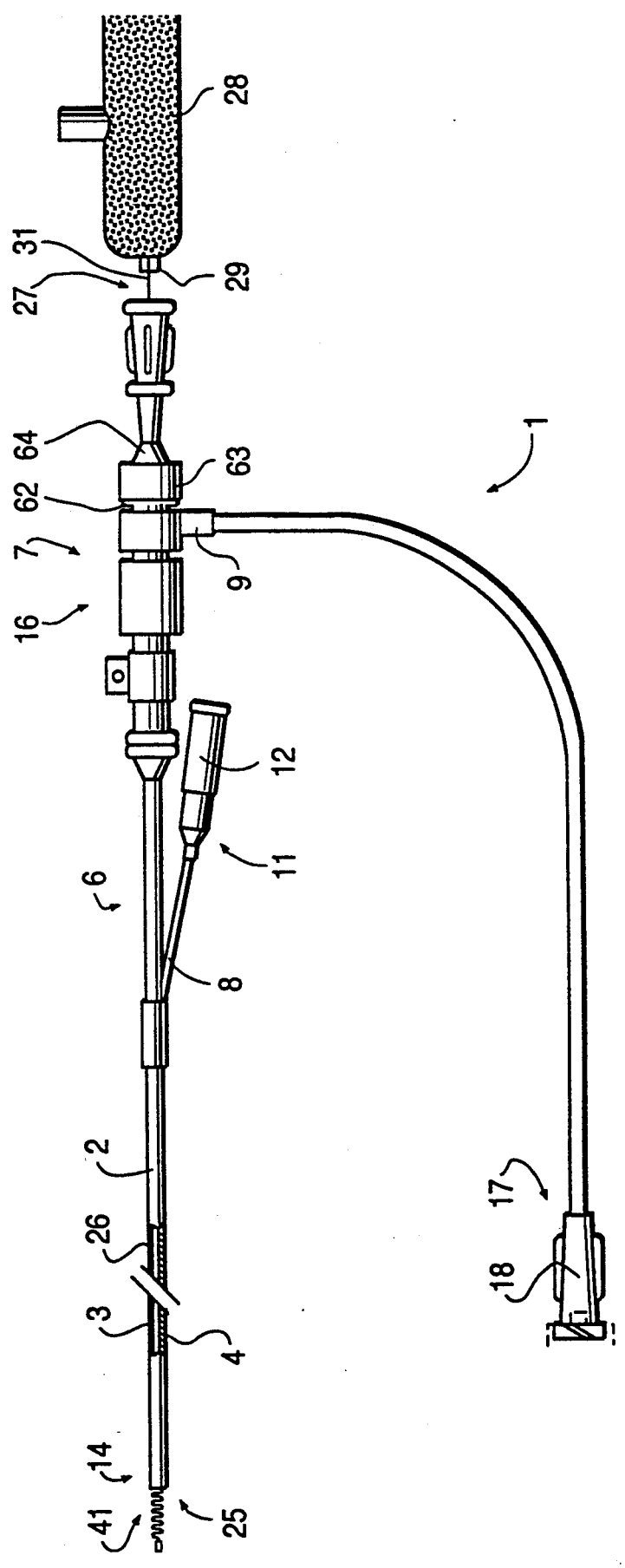
FIG. 1 is a side view, partly in section with a preferred construction of the inventive apparatus.

The apparatus for removing deposits from vessels or organs, such as blood vessels or the gall bladder shown in FIG. 1 has as the guidance part 2 a plastic catheter, which, in the represented embodiment, has two lumens with a main lumen 3 filling virtually the entire cavity of the catheter 2 and a further lumen 4 with a much smaller cross-section.

In the proximal region 6 the guidance part 2 is provided with two branches 8, 9 laterally of the proximal end 7. The branch 8 issues into the lumen 4 and has at its proximal end 11 an adaptor 12 for the fitting of a syringe or the like enabling striptokinase or the like to be forced through the lumen 4 to the distal end 14 of the guidance part 2 and out of the latter in order to partly dissolve the deposits.

The other branch 9 is connected to the main lumen 3 of guidance part 2. A suction device is connected by an adaptor 18 to its end remote from the guidance part 2 in the connection area 16 for suctioning deposits separated or crushed in a manner to be described hereinafter from the vessel or the organ. The suction device can in its simplest form be a medical syringe, which is drawn on by the surgeon or his assistant. In a particularly preferred manner the suction device is a motor-driven and in particular electrically driven pump. The suction rate is variable, namely adjustable, controllable or regulatable. In particular the quantity suctioned out of the main lumen 2 can be varied.

The face of the guidance part 2 is sealed with a seal, in the manner known from WO-A-86/06951. For this purpose the guidance part 2 can be provided at the proximal end 7 with a Luer Adaptor or the like.

In preferred manner the seal is constructed in such a way that in a sleeve part 62 positioned proximally of the branch 9 of a valve part 61, such as a hemostatic valve is arranged a hose part, whose diameter in the unloaded state is such that a helical attachment 41 constructed as a wire and located at the distal end 25 of a driving shaft 26 located in the guidance part 2 can be inserted freely through the hose part. The internal cross-section of the hose part is consequently at least as large as the cross-section of the helical attachment 41 in the unloaded state.

The sleeve attachment 62 is provided with an external thread and on it is located a cap 63 having an internal thread. With its end face 64 and if screwed to the branch 9 the cap 63 presses together the hose part, so that the latter is applied to the shaft 26 and forms a reliable seal. The shaft 26 can be moved axially backwards and forwards under friction.

Thus, the shaft 26 projects through the main lumen 3 of the guidance part 2 and its proximal end 27 is passed through the seal 22, with the sealing between the seal 22 and the shaft 26 being maintained. The proximal end 27 is connected to a drive 28.

For connection purposes it is possible to provide appropriate drill receptacles 29, with the reception area 31 of the shaft 26 not having a larger, or at least significantly larger cross-section than the shaft over its entire length, so that the proximal end 27 of the shaft 26 can e.g. be inserted from the side of seal 22, which faces the same after fitting it to the guidance part 2 through a seal in accordance with WO-A-86/06951. The shaft 26 is then subsequently introduced with the seal positioned on it into the guidance part 2 (from the proximal end 7). The seal passes into the adaptor and is fixed therein in the represented manner by a clamping part connectable to the adaptor, which ensures a reliable seal.

Independently of the nature and the construction of the seal and the passing through of the helix through the same, the shaft 26 and the clamping attachment 29 of the motor 28 can be subsequently interconnected. As shown, the motor can be a free hand-holdable hand motor. It can also be connected to the adaptor in the clamping part, so that it is held in non-rotary manner by the latter and the seal could then be provided in the connecting area.

In the case of the aforementioned construction of the proximal end 27 of the shaft 26 and the use described in connection therewith, the helical attachment 41 is constructed in one piece with the shaft 26. Alternatively, the shaft 26 and the helical attachment 41 can be interconnected by adaptor parts and the latter can also be constructed in per se known manner. The adaptor area of the shaft 26 can have a cross-section not exceeding the thickness of said shaft 26 and could e.g. be formed by an external thread on the distal end 25 of the shaft 26, with the adaptor part of the helix 41 being a sleeve with an adapted internal thread. The thread direction of such adaptor parts is such that the threaded connection is not released in the normal rotation direction of the motor 28 and instead tends to tighten.

If from its transition or connecting region with the shaft 26, i.e. from this proximal end, the helical attachment 41 forms a right-handed screw, then on consideration from its proximal end 27, the shaft 26 must also rotate to the right, i.e. clockwise. Thus, then the external thread on the distal end 25 of the shaft 26 is a right-handed thread. Therefore, the thread direction corresponds to the rotation direction of the helical attachment 41 when considered in the same direction.

The helical attachment 41 is made from a very rigid, helically shaped material while leaving free in its interior a free space 48 surrounded by the individual turns 47 or the internal spheroid thereof. The distal end 49 of the helical attachment 41 is truncated, e.g. by bending to form a figure of eight 51, as shown in the drawing. The outer area of the individual turns 47 is also truncated and preferably rounded. Stiff wire rod material can be used for the helical attachment 41.

In place of a cylindrical construction of the helix 41, it is also possible to provide helical attachments constructions tapering conically towards the distal end 49. The distal region 49 of the helical attachment 41 could also be laterally bent away with respect to its connecting region 42 to the shaft 26 and therefore the axis of the latter.

Figure 2:
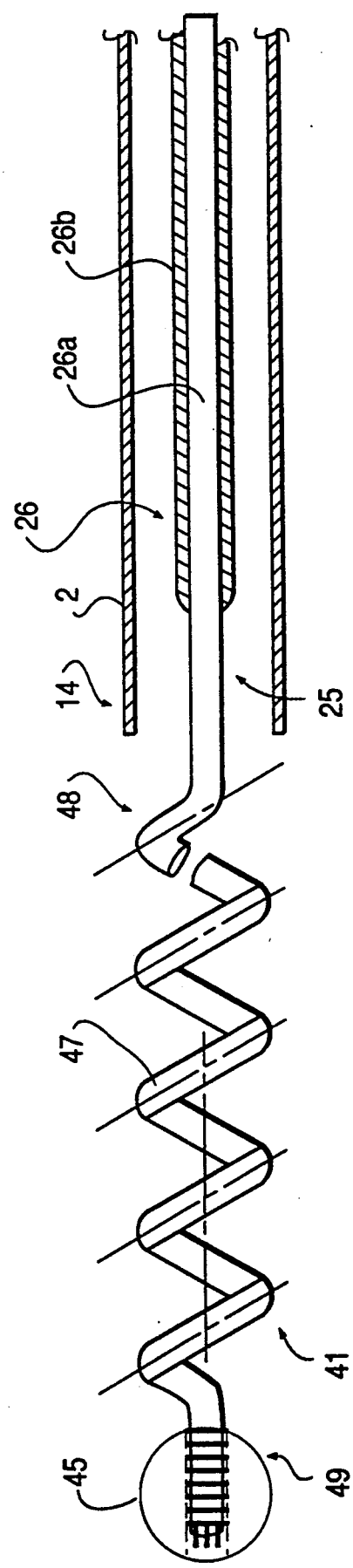
FIG. 2 is an enlarged partial cross-sectional detail view of the apparatus of FIG. 1 with a ball positioned upstream at the distal end.

FIG. 2 shows a preferred construction with a helical attachment 41 having a constant cross-section over its length or height. However, instead of this the helix can taper towards the distal end. With its proximal end the helical attachment 41 passes in one piece into the shaft 26. The helical attachment 41 is provided with a ball 45 at the free distal end and the ball can be welded to attachment 41. However, it could also be connected thereto by a screw connection. The helical attachment 41 is constructed in one piece with the core 26a of the shaft 26 extending to the driving motor 28. For stiffening purposes and proximal with respect to the helix 41, the shaft 26 is additionally provided with a sleeve 26b surrounding the core 26a and which also extends up to the motor 28. The core 26a and sleeve 26b are preferably welded together. The ball 45 has a diameter which, like the diameter of the helix 41, is slightly smaller than the internal lumen of the guidance part 2. As a result of this ball construction, and which, as a result of its inertia and the flexibility of the shaft 61 moves about a fulcrum located outside its center, residues or deposits can be crushed. They are then suctioned by the vacuum applied to the guidance part 2 and are lead through the screw construction 63 to the proximal end.

Figure 3:
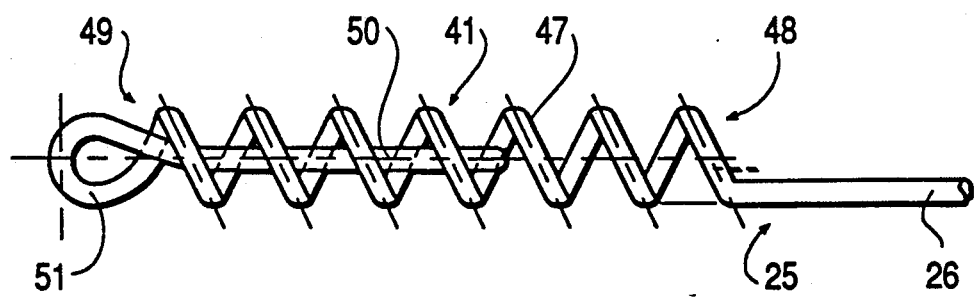
FIGS. 3-7 are schematic views of different constructions of helix arrangements.

In the FIG. 3 the ball is replaced by bending the free distal end 49 of the helical attachment 41 into a (partial) figure eight 51 and a straight end portion 50 is lead back into the interior of the helix.

Figure 4:
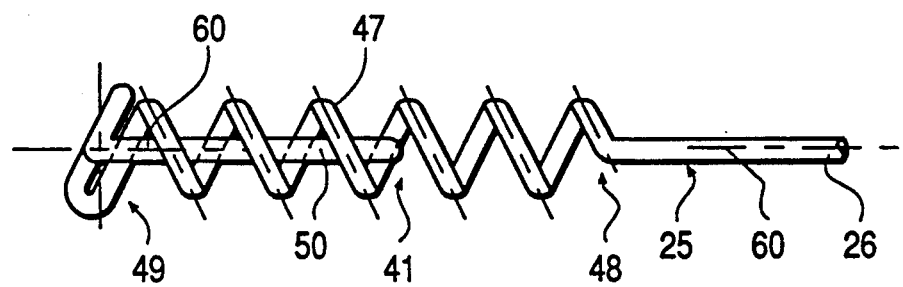

FIG. 4 shows a helix 41 with a constant cross-section over its length, in which the distal end 49 is in one plane, whose normal line forms an angle of <90°, preferably <45° and, in the represented embodiment, approximately 20° to 25° with the axis 60 or driving shaft 26. In this construction, the distal end 49 extends radially over and beyond the thickness of the helix 41. Such a distal end 49 could also be constructed as a figure eight located in the plane. Instead of this the end face formed by the helical wire can be at right angles to the axis 60, so that its normal coincide with the latter.

Figure 5:
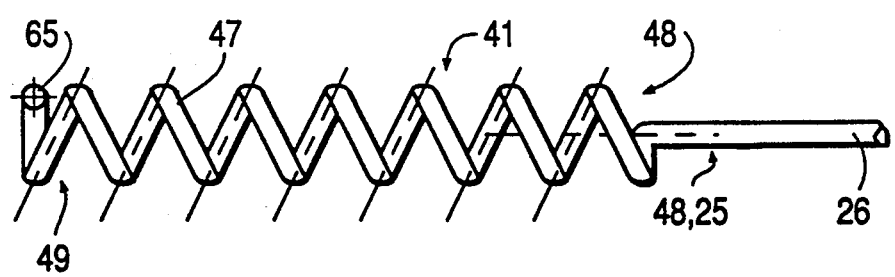

The construction according to FIG. 5 has a constant cross-section over its length and once again the helix could taper towards the distal end. The helical wire in this case terminates in a distal manner without any special construction of the distal region 49. However, the end face 65 of the free end of the wire should be truncated, by abrading burrs.

Figure 6:
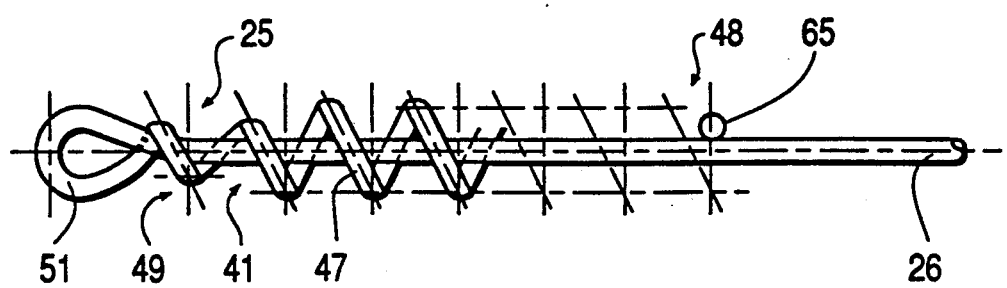

The construction according to FIG. 6 tapers towards the distal end and there could also be a constant cross-section over the helix height. The distal end of the helix 41 is shaped like a (partial) figure eight 51. The difference between this construction and that of FIGS. 1 to 3 is essentially that the shaft 26 is extended with its distal end 25 and to the latter is connected the (partial) eight 51 and the helix 41 is then wound around the distal end 25 of the shaft 26 and its proximal end 48, the free end terminating in a similar manner to FIGS. 6 and 7, but in a proximal manner.

Figure 7:
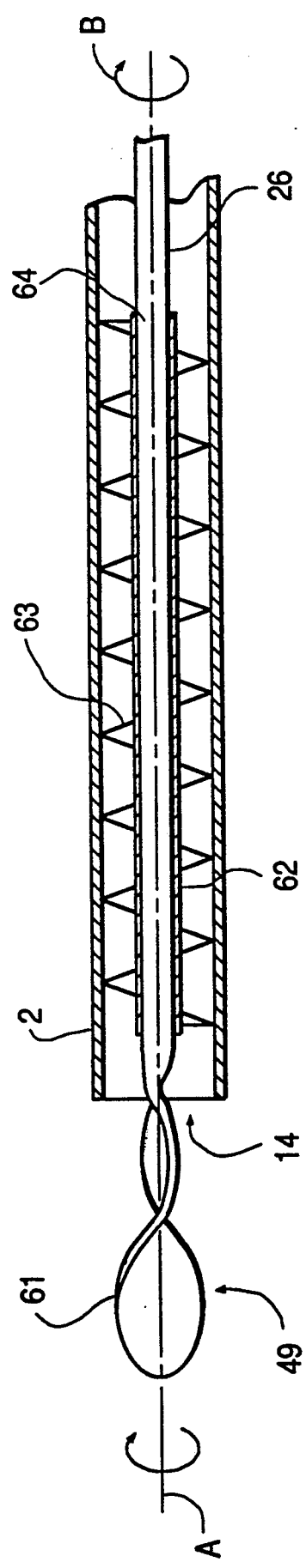

FIG. 7 shows another helix construction, which is once again to be considered in conjunction with the other features of FIG. 1. In this construction the driving shaft 26 is constructed in one piece. It continues in one piece up to its proximal end 27 by which it is connected to the motor (cf. FIG. 1). It is provided at its distal end with a blade-like widened portion 26, which is turned or twisted about the axis A of the shaft 26, which leads to a part helical construction of the widened portion 61. In the proximal direction following on to the widened portion 61 a sleeve 62 is located on the shaft 26 and its internal diameter substantially corresponds to the external diameter of the shaft 26 and which is provided here on its outside with a helical construction in the form of a screw thread 63. The twisted widened portion 61 and the screw construction 63 rise in the same direction in such a way that deposits comminuted by the portion 61 and conveyed towards the inlet of the distal end of the guidance part 2 are conveyed in the proximal direction through the rotation direction by the screw construction 63 within the guidance part 2. The sleeve 62 is fixed to the shaft 26, e.g. by welding points 64.

In a variant of the above construction the blade-like widened portion 61 may be replaced by a ball 45 such as shown in FIG. 2 connected to the shaft 64.

Other constructions are also conceivable, in which e.g. widened portions 61 and screw constructions 63 are constructed in one piece and optionally also with the shaft 26.

In a preferred manner the helixes 41 have approximately 5 to 10 individual turns 47. The diameter of the helixes 41, 61 is determined as a function of the intended use and is approximately 1 to 2 mm, but can also be somewhat larger. The wire thickness is in the submillimeter range. The helix length is a few centimeters, typically 1 to 3 cm and preferably 1 to 2 cm. Use is preferably such that the helix 41 does not project entirely out of the distal end 14 of the guidance part 2 and instead, as shown in FIG. 1, extends partly into the guidance part 2, so that on rotating the helix and the feed action exerted by it deposit fragments are fed into the guidance part 2 and are reliably taken up there during suction.

In place of the helix construction 63, they can also have the form of a helical brush arranged on the sleeve 62 and provided with radially extending bristles (not shown). This also assists the transfer to the proximal end of the sleeve of the deposit fragments which have been crushed and received in the distal reception end 14 of the sleeve.

The invention preferably functions as follows. In order to remove deposits in a blood vessel, the latter is initially punctured at an appropriate point, subsequently a guide wire is introduced through the puncture cannula into the blood vessel, the cannula is drawn over the proximal end of the wire, then a catheter instrument is introduced and with it the guidance part 2 serving as the suction catheter together therewith or subsequently. The shaft 26 with the helical attachment 41, 61 can be located in the guidance part 2, but retracted into the cavity, or can be subsequently inserted. The shaft 26 with the helical attachment 41, 61 is partly moved out of the distal end 14 of the guidance part 2, preferably by 3 to 10 mm and, in particular, 3 to 5 mm and then the suction device and driving motor 28 are put into operation. The motor typically rotates at 20,000 r.p.m. Thus, by the helical attachment 41, 61 the deposits in the vessel are removed and said through attachment 41, 61 to the distal opening of the guidance and suction part 2, where the deposits are then removed by the suction device, such as a syringe, centrifugal pump, etc. and is therefore suctioned out of the working area of the helical attachment 41, 61. Prior to the start of mechanical removal and during the same, the deposits can be partly dissolved in the described manner by injecting streptokinase.

In order to remove a gallstone the gall bladder is percutaneously transhepatically punctured. After applying the guide wire and removing the puncture cannula, the skin area is dilated and a catheter is passed over the guide wire to the gall which, if the wire is located in the secondary lumen, can already contain the shaft. Otherwise it is inserted following the removal of the guide wire. Then, in the manner described hereinbefore, the guidance and suction part 2 and the shaft 3 with helical attachment 41, 61 are inserted. Insertion preferably takes place under X-ray or ultrasonic examination. In the first case a radio-opaque agent is firstly injected, which can also take place through the guidance part. The distal end 49 of the helical attachment 41, 61 is placed on the gallstoane and the motor started. In this case preferably a conical helical attachment 41 (e.g. FIGS. 3/7) is used. As a result of the high rotational speed it can bore into the stone (whose inertia and frictional forces prevent it from rotating at the same speed), so that the stone can be shattered, particularly in the case of a conical helical attachment construction. The parts are substantially crushed and the pasty fragments are suctioned off by the suction device, so that fragments cannot pass into the individual ducts (such as the ductus choledochus and ductus pankreaticus), where inflamation can be caused. Fundamentally an endoscopic approach to the gall is possible. The inventive drive 1 as shown in FIG. 8-11 has a casing 72, which houses an electric motor and a power supply, such as a battery or an accumulator and which can be inserted as a battery or an accumulator and which can be inserted in the casing through opening 74. The casing also contains a speed regulator for the motor, which is controllable by means of a setting knob 76, so that the speed can be set and adjusted in desired ranges, e.g. between 0 and 2,000 r.p.m. or higher. The casing also contains a display 77, in this case a LCD, which shows the amount of power of the power supply means which has been consumed and therefore when a replacement is necessary. The drive 71 is also provided with an on/off switch for switching the rotary drive on and off. On the front of the drive 71 a bridge 79 is provided on the casing 72 and at its end remote from the latter, namely at 81 has an opening 82 which is open from the top with undercut, lateral grooves 83 and into which are insertable the radial flanges on a hollow guide part, such as a suction catheter, so that the latter can be fixed relative to the drive 71 and in particular its casing 72, more especially in the axial direction.

Into the space surrounded by the catheter holding bridge 79 projects a connecting part 10 with a driving shaft 84, which is provided at its free end with a connecting attachment 86, such as e.g. a male Luer-Lok. By the female Luer-Lok part can be connected in non-rotary manner a device for removing deposits by the rotation thereof, such as a rotational spiral. The said device has over its length roughly corresponding to that of the hollow guide part or catheter, a straight shaft and can be provided at its proximal end, i.e. the end remote from the drive 71, with a helical construction, as well as following onto the latter a ball with or without a cutting edge means, or with a radially spreadable basket-like member, optionally with a cutting edge means.

On the top of the casing is provided a slide part 87, to which is connected the shaft 84 so as to be rotatable, but axially fixed with respect thereto. The shaft 84 is once again in axial, but non-rotary engagement with a driven stub of the motor located in the casing 72.

Figure 8:
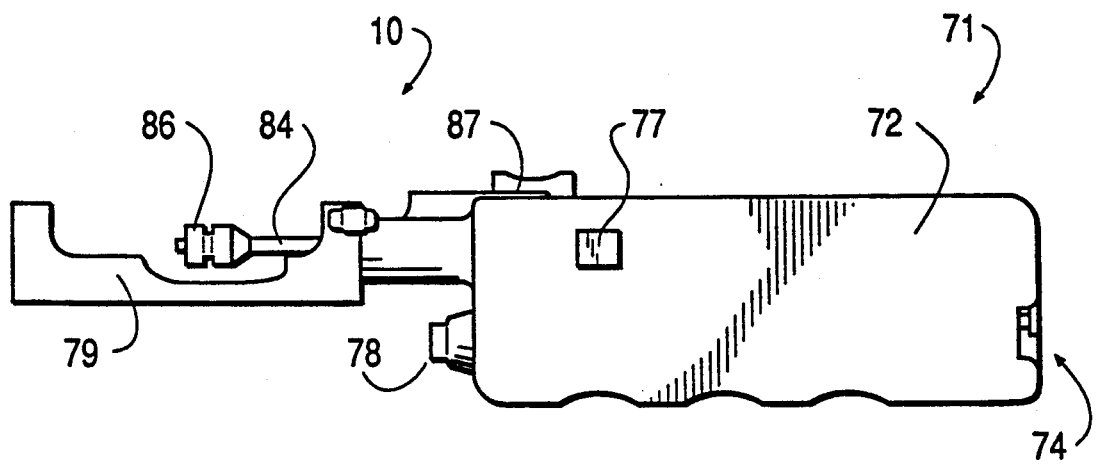
FIG. 8 is a schematic side view of the inventive drive.
Figure 9:
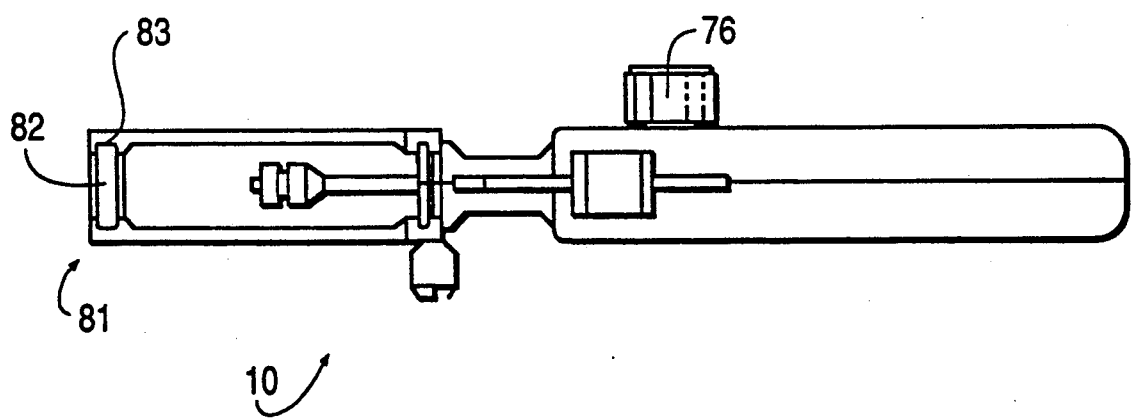
FIG. 9 is a plan view of FIG. 1.
Figure 10:
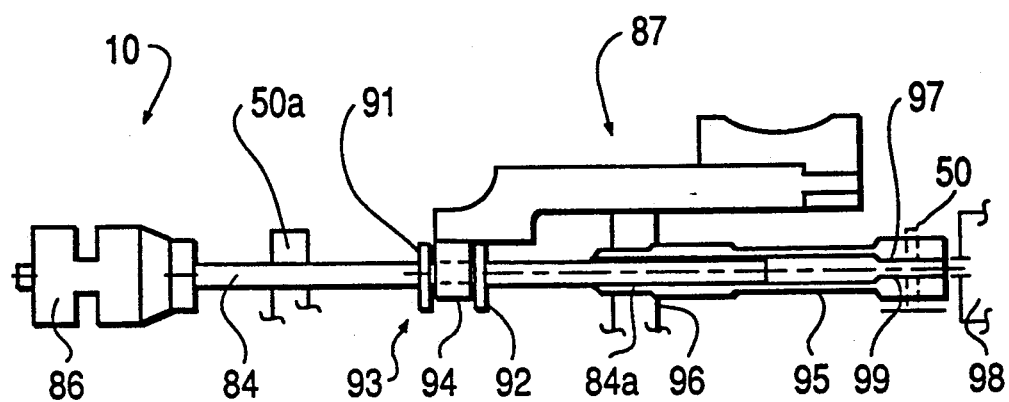
FIG. 10 is a schematic view of a preferred embodiment of coupling of a linear drive to the medium-speed rotary drive.

A specific embodiment of this connection is shown in FIG. 8. The driving shaft 84 carries at its front end in non-rotary manner the Luer-Lok 86. It also has non-rotary radial flanges 91, 92 which are spaced from one another and which can e.g. be constructed on an engaged sleeve 93, such as a brass sleeve soldered to the shaft 84. A C-shaped part 94 engages between the flanges 91, 92 on the shaft 14 or the sleeve 43 connected thereto, while ensuring rotation. This part 94 is snapped over the shaft 94 or the sleeve 93 and is firmly connected to the slide part and is e.g. constructed in one piece therewith.

On the other side of the flanges 91, 92 the shaft 84 projects into a guide sleeve 95, which is mounted in rotary manner relative to the casing by means of a bearing 96. At the end of the guide sleeve the driven shaft 97 of a motor 98 projects into the sleeve 95 and is connected in non-rotary manner thereto by a pin 50 passing through transverse bores 99. The cross-section of the part 84a of shaft 84 projecting into the guide sleeve 95, as well as the internal cross-section of sleeve 95 are not circular, but instead have a shape differing from the circular, e.g. flattened, so that the shaft 84 can also be rotated by the guide sleeve 95 driven by the motor 98. The shaft 84 is also guided by a bearing 50a with respect to which it is displaceable and rotatable.

As a result of the described construction the rotary drive of the shaft 84 by the motor 98 and the axial displaceability of the shaft 84 relative to and in the sleeve 45 are ensured.

Figure 11:
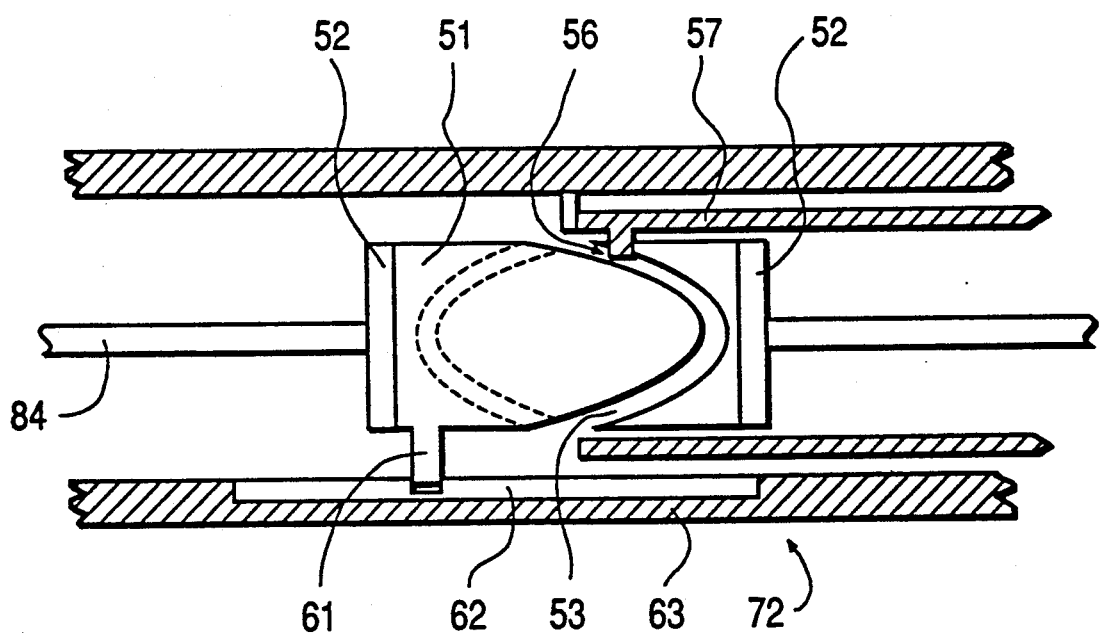
FIG. 11 is a schematic partial cross-sectional view of an embodiment for a motor reciprocating linear drive of the connecting part.

FIG. 11 diagrammatically shows an embodiment for transforming the linear reciprocating movement derived from the rotary drive for the connecting part. The driving shaft 84 of the connecting part 10 is rotatable, but is axially fixed to a sleeve 51, similar to sleeve 93, e.g. by radial flanges 52 firmly engaging on the driving shaft 84 of the connecting part 10 on either side of the sleeve 51. In order to reduce friction, it is possible to provide within the sleeve 51 between the latter and the driving shaft 84 a conventional bearing means. In the outer circumference of the sleeve is provided a closed groove, which passes in meander-like manner from one face of the sleeve and then around the same and back to the first face. The cam 56 of a further sleeve 57 engages in the groove. So that the sleeve 51 does not rotate with the sleeve 57, it is guided by means of a cam 61 in a groove 62 of the wall 63 of the casing 2 or a part firmly connected thereto. During the rotation of the sleeve 57 the cam 56 is urged against the wall of the groove 53 of the sleeve 51 inclined with respect to its rotation direction. As the sleeve cannot rotate with it due to its linear guide 61, 62, it is axially displaced by the cam 56 until the latter arrives at one of the reversal points of the groove 53 at the faces of sleeve 51, where the linear movement is then reversed. By the flanges 52 the sleeve 51 takes the driving shaft 84 with it during its reciprocating movement. The rotary drive of the rotary sleeve 57 can be derived from the rotary drive of the motor and, as the reciprocating movement of the sleeve 51 and therefore the rotary movement of the sleeve 57 is much smaller than the rotary movement of the motor, by means of a reduction gear, which can e.g. be constructed in the form of a sun gear-planet gear with an annular gear constructed in the sleeve 57, in the form of clockwork motions or the like. The rotary drive of the shaft 14 and therefore the connecting part 10 takes place in the same way to that which has been described relative to FIG. 10.

We claim:

1. An apparatus for the removal of deposits, such as patches in vessels and stones in organs of animals, the apparatus comprising:
   a hollow guidance part;
   a drive means;
   a shaft driven by the drive means and projecting into the hollow guidance part;
   a helical portion provided on a distal end of the driving shaft at least partly projecting out of a distal end of the hollow guidance part, said helical portion having a cross-sectional dimension not greater than an internal dimension of the hollow guidance part, individual turns of the helical portion have a finite spacing with respect to one another, said individual turns surround a free space within the helix whereby deposits received between the individual turns of the helical portion are lead by the individual turns through said free space to a distal end of the hollow guidance part;
   a sleeve connected firmly and in a rotary manner to the connecting part and in a non-rotary manner to a drive casing and having a closed meandering groove guided around a circumference of the sleeve and;
   a cam of a transmission part rotating at a lower angular velocity than an angular velocity of the connecting part engageable in said groove, wherein the drive means includes means for receiving one end of the hollow guidance part, a rotary drive rotatably driving the helical portion, and a rotary connecting part axially reciprocatable relative to the hollow guidance part by a motor means.

2. Apparatus according to claim 1, wherein the distal end of the driving shaft includes a blade-like widened portion.

3. Apparatus according to claim 2, wherein the blade-like widened portion is bent about an axis of symmetry of the shaft in a screw shape.

4. Apparatus according to claim 1, wherein the guidance part includes a lumen for receiving the shaft, and wherein a branch is provided on the lumen for enabling a connection to a suction device.

5. Apparatus according to claim 1, wherein the guidance part includes a main lumen with a cross-section taking up substantially an entire internal cross-sectional area of the guidance part and a secondary lumen having a cross-section less than the main lumen, and wherein a branch for accommodating a syringe is provided at a proximal end of the secondary lumen.

6. Apparatus according to claim 1, wherein the helical portion is introducible through the guidance part into a vicinity of a deposit and rotated so as to enable a removal of the deposit.

7. Apparatus according to claim 1, wherein a receptacle is provided on the rotary connecting part.

* * * * *